United States Patent [19]

Newton et al.

[11] Patent Number: 5,508,251

[45] Date of Patent: Apr. 16, 1996

[54] HERBICIDAL METHODS AND COMPOSITIONS COMPRISING EPOXY COMPOUNDS

[75] Inventors: Trevor W. Newton, Schwabenheim, Germany; Binne Zwanenburg, Malden, Netherlands

[73] Assignee: American Cyanamid Company, Madison, N.J.

[21] Appl. No.: 288,536

[22] Filed: Aug. 10, 1994

[30] Foreign Application Priority Data

Aug. 11, 1993 [EP] European Pat. Off. .............. 93112867

[51] Int. Cl.$^6$ .......................... A01N 43/20; C07D 303/38
[52] U.S. Cl. .............................................. 504/291; 549/549
[58] Field of Search ........................... 504/291; 549/549; A01N 43/20

[56] References Cited

U.S. PATENT DOCUMENTS

| | | | |
|---|---|---|---|
| 2,939,872 | 6/1960 | Hudson | 260/348 |
| 2,993,058 | 7/1961 | Hudson | 260/348 |
| 3,136,788 | 6/1964 | Payne et al. | 260/348 |
| 3,930,835 | 1/1976 | Ozretich | 71/88 |
| 4,211,549 | 7/1980 | Markley et al. | 71/88 |
| 4,849,007 | 7/1989 | Rempfler et al. | 71/76 |

FOREIGN PATENT DOCUMENTS

| | | |
|---|---|---|
| 0225290 | 6/1987 | European Pat. Off. . |
| 857126 | 12/1960 | United Kingdom . |
| 2120235 | 2/1983 | United Kingdom . |
| 2200628 | 8/1988 | United Kingdom . |

OTHER PUBLICATIONS

Biorganic Chemistry, vol. 21, No. 4, Dec. 1993, New York, pp. 367–385, D. H. Flint et al. "Studies on the Active Site of Dihydroxy–acid Dehydrates".

Journal of Organic Chemistry, vol. 54, No. 7, Mar. 31, 1989, Easton, Pa. pp. 16543–1562, Pirrung et al., "Purification and Inhibition of Spinach alpha, beta–Dihydroxyacid Dehydratase".

Bulletin Des Societes Chimiques Belges, vol. 65, 1956, Oxford, GB, pp. 664–674, G. Chiurdoglu et al., "Composes Alicycliques A Carbone Quaternaire, V. Synthese et Spectres Infra–rouge de Quelques 2–ethoxycarbonyl–1–oxacuclopropane–spiro-cyclanes".

Thus, et al., "Synthesis of α,β–Epoxy Diazomethyl Ketones", *Pergamon Press Ltd.*, 36,: pp. 2141–2143 (1980).

*Primary Examiner*—S. Mark Clardy
*Attorney, Agent, or Firm*—Charles F. Costello, Jr.

[57] ABSTRACT

A method of combating undesired plant growth at a locus is disclosed, the method comprising applying to the locus a compound of general formula:

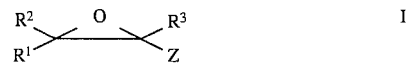

where $R^1$ and $R^2$ independently represent a hydrogen atom or an optionally substituted alkyl or alkenyl group or $R^1$ and $R^2$ together represent an optionally substituted alkyl or alkenyl chain;

$R^3$ represents an optionally substituted saturated or unsaturated homocyclic or heterocyclic group; and Z represents a group —COOR$^4$ where R$^4$ represents a hydrogen atom, a cation or an optionally substituted alkyl, alkenyl, alkynyl or aryl group, or Z represents a group —CHO.

The use of a compound of general formula I as a herbicide and a herbicidal composition are also disclosed.

10 Claims, No Drawings

HERBICIDAL METHODS AND COMPOSITIONS COMPRISING EPOXY COMPOUNDS

This invention relates to methods of combating undesired plant growth and to herbicidal compositions. The invention employs substituted epoxy compounds.

α,β-Epoxydiazomethyl ketone compounds and methods of preparation thereof are disclosed in Tetrahedron, 36, 2141, (1980). No use of the compounds is disclosed.

U.K. Patent Application GB 2 120 235 (Imperial Chemical Industries plc) discloses triazole and imidazole derivations having fungicidal and plant growth regulating activity. A broad class of substituted epoxy compounds is disclosed as intermediates in the preparation of the triazole and imidazole derivatives. No other use of the substituted epoxy intermediates is disclosed.

This invention is based upon the discovery of a class of substituted epoxy compounds that have been found to exhibit herbicidal activity.

In accordance with a first aspect of the present invention, there is provided a method of combating undesired plant growth at a locus, comprising applying to the locus a compound of general formula:

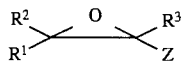

where $R^1$ and $R^2$ independently represent a hydrogen atom or an optionally substituted alkyl or alkenyl group or $R^1$ and $R^2$ together represent an optionally substituted alkyl or alkenyl chain;

$R^3$ represents an optionally substituted saturated or unsaturated homocyclic or heterocyclic group;

and Z represents a group —COOR$^4$ where $R^4$ represents a hydrogen atom, a cation or an optionally substituted alkyl, alkenyl, alkynyl or aryl group, or Z represents a group —CHO.

Compounds of general formula I may exist in a number of stereo-isomeric forms and all such forms fall within the scope of the present invention.

Generally, when any of the above mentioned moieties comprises an alkyl group, the alkyl group may be linear or branched and may suitably contain 1 to 10, preferably 1 to 6, and most preferably 1 to 4 carbon atoms, suitable examples being methyl, ethyl and propyl. When any groups are designated as being optionally substituted, the substituent groups which are optionally present may be any of those customarily employed in the development of pesticidal compounds, and/or the modification of such compounds to influence their structure/activity, persistence, penetration or other property. In, relation to moieties defined above which comprise an optionally substituted alkyl or alkenyl group, specific examples of such substituents include halogen, especially fluorine, chlorine or bromine atoms, and nitro, cyano, hydroxyl, $C_{1-4}$ alkoxy, $C_{1-4}$ haloalkoxy, ($C_{1-4}$ alkoxy)carbonyl groups, amino and $C_{1-4}$ alkylamino groups; and, in relation to an alkenyl group, oxo groups. It is preferred, however, that alkyl moieties are unsubstituted, or halogen-substituted and that alkenyl moieties are unsubstituted, or only substituted by alkyl. In relation to moieties defined above which comprise an optionally substituted saturated or unsaturated homocyclic or heterocyclic group, optional substituents include halogen, especially fluorine, chlorine and bromine atoms, and nitro, cyano, amino, hydroxyl, $C_{1-4}$ alkyl, $C_{1-4}$ haloalkyl (especially $CF_3$) and $C_{1-4}$ alkoxy groups. 1 to 3 substituents may suitably be employed.

$R^1$ and $R^2$ may independently represent a hydrogen atom, an optionally substituted alkyl group or together represent an optionally substituted alkyl chain. Preferred optionally substituted alkyl groups include 1 to 4 carbon atoms, with optionally substituted methyl, ethyl, iso-propyl and iso-butyl being especially preferred. A preferred optionally substituted alkyl chain has a general formula —(CH$_2$)$_n$— where n is 4 or, more preferably, 5.

$R^1$ and $R^2$ may be the same or different. Preferably, $R^1$ and $R^2$ represent the same atom or group.

Preferably, $R^1$ and $R^2$ independently represent a hydrogen atom or an optionally substituted, more preferably an unsubstituted, methyl group. Interesting herbicidal activity has been noted wherein $R^1$ and $R^2$ both represent a methyl group.

$R^3$ may represent an optionally substituted aryl or heteroaryl group. Preferably, $R^3$ represents an optionally substituted aryl group. A preferred optionally substituted aryl group is an optionally substituted phenyl group.

Where $R^3$ represents a substituted phenyl group, said phenyl group is preferably substituted in the 4-position relative to the linkage. Said optionally substituted phenyl group may be unsubstituted or mono-substituted; it is preferably mono-substituted. Preferred substituents of said phenyl group include an alkyl group, especially a methyl group, an alkoxy group, especially a methoxy group, a halogen atom, especially fluorine and chlorine atoms, and a nitro group. Where said phenyl group is substituted by a halogen atom, it is preferably substituted by a chlorine atom.

$R^3$ preferably represents a 4-methylphenyl or 4-chlorophenyl group. More preferably, $R^3$ represents a 4-chlorophenyl group.

Z may represent a group —COOR$^4$, where $R^4$ is as described above. Where $R^4$ represents a cation, it preferably represents an alkali metal cation, for example, Li$^+$, Na$^+$ or K$^+$. A preferred alkali metal cation is Na$^+$.

Preferably, Z represents a group —COOR$^4$, where $R^4$ represents a hydrogen atom, a cation of sodium (Na$^+$) or an alkyl group, especially an ethyl group. Most preferably, Z represents a group —COO Na$^+$.

In a method as defined above, the dosage of the active ingredient in the compound of general formula I, may, for example, be from 0.01 to 10kg/ha, suitably 0.05 to 4kg/ha. The locus may be an agricultural or horticultural locus, comprising, for example, a plant or soil. In a preferred method the locus contains undesired plant growth and treatment is by foliar spray application.

The invention also provides the use of a compound of general formula I as defined above, as a herbicide.

In accordance with a further aspect of the present invention there is provided a herbicidal composition comprising a compound of general formula I as defined above, in association with at least one carrier which is a surface-active agent. Preferably there are at least two carriers, at least one of which is a surface-active agent.

A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively higher concentration of active ingredient. Emulsifiable concentrates usually contain, in addition to a solvent and, when necessary, cosolvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

The invention further extends to a compound of general formula I, wherein $R^1$ and $R^2$ represent a methyl group, $R^3$ represents a 4-halophenyl group, preferably a 4-chlorophenyl group, and Z represents a group —COONa per se.

Said compounds of general formula I as described above may be prepared by reacting a compound of general formula

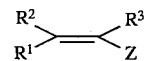
II where $R^1$ $R^2$ $R^3$ and Z are as described above, with an oxidizing agent adapted to epoxidate the compound of general formula II, and optionally derivatising the product of the reaction.

A preferred oxidizing agent is a per-acid, for example m-chloroperbenzoic acid.

The reaction of said compound of general formula II with an oxidizing agent is suitably carried out in the presence of a catalytic amount of iodine, in an organic solvent, for example dichloromethane, and at an elevated temperature.

When in said compound of general formula I, Z represents a group —COOR$^4$ where R$^4$ represents a cation, a compound of general formula II, where Z represents a group —COOR$^4$ and R$^4$ represents an optionally substituted alkyl group, preferably a methyl group or an ethyl group, is suitably oxidized as described above. The product may then be derivatised by reaction with a hydroxide of said cation, for example sodium hydroxide, suitably in an alcoholic solvent, and under reflux.

Said compound of general formula II is suitably prepared by reaction of a compound of general formula

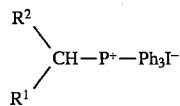
III in the presence of a strong base, with a compound of general formula

IV wherein $R^1$, $R^2$, $R^3$ and Z are as described above

The reaction of compounds of general formula III and IV is suitably a Wittig condensation reaction. The reaction is preferably carried out in the presence of an aprotic organic solvent and at a temperature of less than ambient temperature.

Compounds of general formula III are commercially available or may be manufactured by a standard procedure.

Said compound of general formula V may be prepared by reacting a compound of general formula

V with a compound of general formula R$^4$OH where R$^4$ is as described above. The reaction is suitably carried out in the presence of sodium bromide and sulphuric acid.

Said compound of general formula V may be prepared by reacting a compound of general formula

 VI wherein $R^3$ is as described above with cuprous, cyanide. Compounds of general formula VI are commercially available or may be prepared by a standard procedure.

Compounds of general formula I may also be prepared by processes analogous to those described in Tetrahedron, 36, 2141, (1980) and/or as described in UK Patent Application GB 2 120 235 (Imperial Chemical Industries plc).

The invention will now be further described, by way of example.

EXAMPLE 1

Preparation of sodium 2-(4-chlorophenyl)-2,3-epoxy-3-methylbutanoate [$R^1=R^2$=methyl; $R^3$=phenyl; Z=—$CO_2Na$]

Example 1a

Preparation of 4-chlorobenzoyl cyanide

A mixture of 4-chlorobenzoyl chloride (35.0 g, 0.2 mol), cuprous cyanide (27.0 g, 0.3 mol) and phosphorus pentoxide (0.05 g) was heated under reflux for 7 hours. The mixture was cooled and the solid material was removed by filtration. The filtrate was evaporated in vacuo and distilled to give 4-chlorobenzoyl cyanide (13.5 g, 41%) as a colourless liquid—b.p. 53°–54° C./0.1 mm Hg.

Example 1b

Preparation of ethyl 4-chlorophenylglyoxylate

4-Chlorobenzoyl cyanide (13.0 g, 0.079 mol) prepared in Example 1a was added to a stirred mixture of sodium bromide (1.0 g, 0.01 mol) and 80% sulphuric acid (10 ml). An exothermic reaction took place with the formation of a solid yellow mass. Ethanol (50 ml) was added and the mixture was heated under reflux to give a yellow solution. On cooling, a colourless precipitate formed. The mixture was diluted with cold water and extracted with isopropyl ether. The organic extract was washed with water, sodium bicarbonate solution and then again with water and dried over sodium sulphate. Evaporation and distillation of the solution gave the product as a yellow oil (8.2 g, 54%)—b.p. 82°–84° C./0.05 mm Hg.

Example 1c

Preparation of ethyl 2- (4-chlorophenyl) -3-methylbut-2-enoate)

A solution of n-butyl lithium in hexane (20 ml, 0.03 mol) was added dropwise to a stirred solution of ethyl 4-chlorophenylglyoxylate (6.4 g, 0.03 mol) prepared in Example 1b, at −10° C. under nitrogen, during which time an exothermic reaction occurred and a red-brown suspension was formed. A solution of iso-propyltriphenylphosphonium iodide (13.0 g, 0.03 mol) in tetrahydrofuran (10 ml) was then added dropwise to the stirred mixture at −10° C. over 10 minutes. An exothermic reaction occurred and the solution became colourless. Stirring was continued for a further 15 minutes at −10° C. after the addition was complete, and the mixture was then allowed to warm to room temperature and stirred for a further 4 hours at this temperature. The reaction mixture was poured onto ice and extracted with isopropyl ether. The organic solution was evaporated in vacuo. The residue was stirred with isopropyl ether and the precipitate was filtered off. The solution was evaporated in vacuo and the product purified by flash silica column chromatography, eluting with petroleum ether/acetone (9:1) to give the title compound as a yellow oil (4.0 g, 56%).

Example 1d

Preparation of ethyl 2-(4-chlorophenyl)-2,3-epoxy-3-methylbutanoate

A solution of ethyl 2-(4-chlorophenyl)-3-methylbut-2-enoate (11.4 g, 0.048 mol), prepared in Example 1c, m-chloroperbenzoic acid (15.7 g, 0.050 mol) and iodine (0.1 g) in dichloromethane (400 ml) was stirred for 48 hours at 50°–55° c. During this period, the course of the reaction was monitored by analytical thin layer chromatography and three further portions (2.0 g) of m-chloroperbenzoic acid and two further portions (0.1 g) of iodine were added to the mixture. The precipitate which formed during this time was dissolved by the addition of 2N sodium hydroxide solution (40 ml) and iced water (200 ml). The organic phase was then separated and washed with dilute sodium hydroxide solution (100 ml) and then with water (3×200 ml). The solution was dried (sodium sulphate), evaporated in vacuo, and the crude product purified by flash silica column chromatography, eluting with 1,2-dichloroethane, to give the title compound (8.6 g, 71%) as an oil.

Example 1e

Preparation of sodium 2-(4-chlorophenyl)-2,3-epoxy-3-methylbutanoate

A solution of ethyl 2-(4-chlorophenyl)-2,3-epoxy-3-methylbutanoate (3.05 g, 12 mmol), prepared in Example 1d, and sodium hydroxide (0.48 g, 12 mmol) in absolute ethanol (40 ml) was refluxed for 1½ hours. After cooling to room temperature, the precipitate was filtered off and the filtrate was evaporated in vacuo to give a residue. The precipitate and the residue from evaporation were combined and washed with isopropyl ether to give the product (2.40 g, 80%) as white crystals.

Analysis Calculated: C 53.13% H 4.05%. Found: C 52.87% H 4.39%.

EXAMPLES 2 to 20

By processes analogous to the processes described in Example 1, the compounds noted in Table 1 were prepared. For the compounds noted in Table 1, $R^1$ and Z are located cis relative to one another.

Yields and analytical data for the compounds of Examples 1, 7 and 16 to 18 are provided in Table 2, where available.

Yields and analytical data for the compounds of Examples 6, 8 to 15, 19 and 20 are provided in Table 3, where available. The data provided in Table 3 is $^1$H NMR data where "s", "d", "t", "q" and "m" represent the terms "singlet", "doublet", "triplet", "quadruplet" and "multiplet" respectively.

Yields and analytical data for the compounds of Examples 2 to 5 are not available.

TABLE 1

| Compound of Example No. | $R^1$ | $R^2$ | $R^3$ | $Z = -CO_2R^4$ where $R^4$ represents: |
|---|---|---|---|---|
| 1 | methyl | methyl | 4-chlorophenyl | Na |
| 2 | methyl | methyl | 4-methylphenyl | Na |
| 3 | methyl | methyl | phenyl | Na |
| 4 | methyl | methyl | 4-methoxyphenyl | Na |
| 5 | methyl | methyl | 4-fluorophenyl | Na |
| 6 | methyl | methyl | 4-chlorophenyl | ethyl |
| 7 | methyl | methyl | 4-chlorophenyl | H |
| 8 | isopropyl | H | 4-chlorophenyl | ethyl |
| 9 | H | methyl | 4-chlorophenyl | ethyl |
| 10 | H | methyl | 4-chlorophenyl | Na |
| 11 | methyl | H | 4-chlorophenyl | ethyl |
| 12 | H | isopropyl | 4-chlorophenyl | ethyl |
| 13 | methyl/ethyl isomeric mixture | | 4-chlorophenyl | ethyl |
| 14 | —(CH$_2$)$_5$— | | 4-chlorophenyl | ethyl |
| 15 | methyl/ethyl isomeric mixture | | 4-chlorophenyl | Na |
| 16 | —(CH$_2$)$_5$— | | 4-chlorophenyl | Na |
| 17 | H | isobutyl | 4-chlorophenyl | ethyl |
| 18 | H | isobutyl | 4-chlorophenyl | Na |
| 19 | methyl | methyl | 4-nitrophenyl | ethyl |
| 20 | methyl | methyl | 4-nitrophenyl | Na |

TABLE 2

| Compound Example No. | Yield % | mp(°C.) | Elemental Analysis (Calc./Found) | | |
|---|---|---|---|---|---|
| | | | C % | H % | Cl % |
| 1 | 80 | — | 53.13 | 4.05 | — |
| | | | 52.87 | 4.39 | — |
| 7 | 67 | 103–105 | 58.3 | 4.9 | 15.6 |
| | | | 58.3 | 5.0 | 15.5 |
| 16 | 81 | — | 58.2 | 4.9 | 12.3 |
| | | | 57.7 | 5.0 | 12.0 |
| 17 | 57 | oil | 63.7 | 6.8 | 12.5 |
| | | | 63.4 | 6.8 | 12.2 |
| 18 | 68 | — | 56.3 | 5.1 | 12.8 |
| | | | 56.6 | 5.3 | 12.7 |

TABLE 3

| Compound of Example No. | Yield % | m.p. (°C.) | $^1$H NMR |
|---|---|---|---|
| 6 | 71 | oil | in CDCl$_3$ 1.0(3H, s), 1.2(3H, t), 1.4(3H, s), 4.1(2H, q), 7.3(2H, d)7.5(2H, d) |
| 8 | 71 | oil | in CDCl$_3$ 1.0(3H, d), 1.1(3H, d), 1.3(3H, t), 1.5(1H, m), 2.7(1H, d), 4.3(2H, m), 7.3(2H, d), 7.5(2H, d) |
| 9 | 30 | oil | in CDCl$_3$ 1.0(3H, d), 1.2(3H, t), 3.5(1H, q), 4.1(2H, q), 7.3(2H, d), 7.4(2H, d) |
| 10 | 78 | — | in d$^6$ - DMSO 1.0(3H, d), 3.4(1H, q), 7.4(2H, d), 7.5(2H, d) |
| 11 | 8 | oil | in CDCl$_3$ 1.1(3H, d)1.3(3H, t), 3.5(1H, q), 4.2(2H, q), 7.3(2H, d), 7.4(2H, d) |
| 12 | 13 | oil | in CDCl$_3$ 0.8(3H, d), 0.9(1H, m), 1.0(3H, d), 1.3(3H, t), 3.1(1H, d), 4.2(2H, q), 7.3(2H, d), 7.5(2H, d) |
| 13 | 42 | oil | in CDCl$_3$ unseparated mixture of isomers (Z:E = 40:60) E-isomer: 0.9(3H, t), 1.3 (3H, m), 1.4(3H, s), 1.6 (2H, m), 4.1(2H, m), 7.6 (4H, m) Z-isomer: 1.0(3H, s), 1.1 (3H, t), 1.2(2H, m), 1.3 (3H, m), 4.1(2H, m), 7.6 (4H, m) |
| 14 | 68 | oil | in CDCl$_3$ 1.1–1.8(10H, m), 1.2 (3H, t), 4.2(2H, m), 7.3 (2H, d), 7.5(2H, d) |
| 15 | 85 | — | in d$^6$ - DMSO unseparated mixture of isomers (Z:E = 40:60) E-isomer: 0.9(3H, t), 1.4 (3H, s), 1.7(2H, m), 7.2 (2H, d), 7.7(2H, d). Z-isomer: 1.0(3H, s), 1.1 (3H, t), 1.2(2H, m), 7.2 (2H, d), 7.7(2H, d). |
| 19 | 68 | oil | in CDCl$_3$ 1.0(3H, s), 1.3(3H, t), 1.5(3H, s), 4.2(2H, q), 7.8(2H, d), 8.2(2H, d) |
| 20 | 77 | — | in d6 - DMSO 1.0(3H, s), 1.4(3H, s), 7.9(2H, d), 8.3(2H, d) |

Herbicidal Activity

To evaluate their herbicidal activity, compounds described in the above Examples were tested using as representative range of plants: maize, *Zea mays* (Z); rice, *Oryza sativa* (R); barnyard grass, *Echinochloa crusgalli* (G); oat, *Avena sativa* (O); linseed, *Linum usitatissimum* (L); mustard, *Sinapsis alba* (M); sugar beet, *Beta vulgaris* (B) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table 4 below. A blank space in Table 4 indicates a rating 0, and the symbol, indicates that testing was not carried out.

TABLE 4

| Compound of Ex. No. | Soil drench 10 Kg/ha |   |   |   |   |   |   |   | Dosage kg/ha | Foliar Spray |   |   |   |   |   |   |   | Pre-emergence |   |   |   |   |   |   |   |
|---|---|---|---|---|---|---|---|---|---|---|---|---|---|---|---|---|---|---|---|---|---|---|---|---|---|
|   | Z | R | G | O | L | M | B | S |   | Z | R | G | O | L | M | B | S | Z | R | G | O | L | M | B | S |
| 1 | 2 | 8 | 6 | 3 | 8 | 7 | 8 |   | 5 | 8 | 8 | 8 | 8 | 8 | 8 | 9 | 1 | 4 | 8 | 5 | 7 | 5 | 7 | 7 |   |
|   |   |   |   |   |   |   |   |   | 1 | 7 | 7 | 8 | 7 | 8 | 8 | 8 |   |   | 5 | 2 | 4 | 2 | 4 | 4 |   |
| 2 |   | 4 | 6 | 5 | 1 | 5 | 7 |   | 5 | 7 | 7 | 7 | 7 | 7 |   | 8 | 9 | 4 | 2 | * | * | 8 | 3 |   | 7 |
|   |   |   |   |   |   |   |   |   | 1 |   | 6 | 7 | 5 |   | 6 | 8 | 1 |   | * |   | 7 |   |   |   |   |
| 3 |   |   |   |   |   |   |   |   | 5 |   |   |   | 3 | 4 | 6 | 2 |   |   |   |   |   |   |   |   |   |
|   |   |   |   |   |   |   |   |   | 1 |   |   |   |   |   | 2 |   |   |   |   |   |   |   |   |   |   |
| 4 |   |   |   |   |   | 6 | 7 |   | 5 |   | 5 | 5 | 4 | 5 | 7 | 6 |   |   |   |   |   |   |   |   |   |
|   |   |   |   |   |   |   |   |   | 1 |   | 3 | 3 | 1 |   | 4 | 3 |   |   |   |   |   |   |   |   |   |
| 5 |   |   |   | 6 | 5 | 6 |   |   | 5 | 2 | 6 | 6 | 4 | 7 | 7 | 7 | 2 |   |   |   |   |   |   |   |   |
|   |   |   |   |   |   |   |   |   | 1 |   | 4 | 2 |   | 2 | 5 | 3 |   |   |   |   |   |   |   |   |   |
| 6 | 2 |   | 5 | 7 | 1 | 4 | 4 |   | 5 | 5 | 4 | 6 | 7 | 5 | 2 | 6 | 3 | 6 | * | 6 | 7 | 6 | 5 | 5 |   |
|   |   |   |   |   |   |   |   |   | 1 | 1 | 1 | 3 | 6 | 3 |   |   |   | 5 | * | 2 | 7 | 4 | 3 |   |   |
| 7 | 7 | 7 | 7 | 6 | 7 | 7 | 8 |   | 5 | 7 | 6 | 6 | 8 | 8 | 8 | 9 | 6 | 6 | 9 | 9 | 6 | 7 | 7 | 8 |   |
|   |   |   |   |   |   |   |   |   | 1 | 7 | 6 | 8 | 7 | 7 | 7 | 7 | 4 | 4 | 6 | 7 | 3 |   | 4 | 6 |   |
| 8 | 1 |   | 4 |   | 2 | 3 | 5 |   | 5 |   |   | 1 | 1 | 3 | 4 | 5 | 4 |   |   |   |   |   |   |   |   |
|   |   |   |   |   |   |   |   |   | 1 |   |   |   |   |   | 1 |   | 2 |   |   |   |   |   |   |   |   |
| 9 |   |   |   |   |   |   |   |   | 5 | 2 |   | 3 |   | 4 | 3 |   | 3 |   |   |   |   |   |   |   |   |
|   |   |   |   |   |   |   |   |   | 1 |   |   |   |   |   | 1 |   |   |   |   |   |   |   |   |   |   |
| 10 |   |   |   |   |   |   |   |   | 5 | 3 |   |   |   |   |   | 5 |   |   |   |   |   |   |   |   |   |
|   |   |   |   |   |   |   |   |   | 1 |   |   |   |   |   |   |   |   |   |   |   |   |   |   |   |   |
| 11 | * | * | * | * | * | * | * | * | 5 | * | * | * | * | * | * | * | * | * | * | * | * | * | * | * | * |
|   |   |   |   |   |   |   |   |   | 1 | * | * | * | * | * | * | * | * | * | * | * | * | * | * | * | * |
| 12 |   |   |   |   |   | 4 |   |   | 5 |   |   | 7 |   | 4 | 3 | 5 | 3 |   |   |   |   |   |   |   |   |
|   |   |   |   |   |   |   |   |   | 1 |   |   | 1 |   |   | 1 |   | 2 |   |   |   |   |   |   |   |   |
| 13 |   |   |   |   |   |   |   |   | 5 | * | * | * | * | * | * | * | * | * | * | * | * | * | * | * | * |
|   |   |   |   |   |   |   |   |   | 1 |   |   |   |   |   |   |   |   |   |   |   |   |   |   |   |   |
| 14 |   |   |   |   |   |   |   |   | 5 | 2 | 1 | 3 | 1 |   | 3 | 5 | 3 |   |   |   |   |   |   |   |   |
|   |   |   |   |   |   |   |   |   | 1 |   |   |   |   |   | 1 | 2 |   |   |   |   |   |   |   |   |   |
| 15 | 6 | 6 | 4 | 2 | 2 | 6 | 9 |   | 5 | * | * | * | * | * | * | * | * | 4 | 5 | 4 | 1 | 4 | 4 | 7 |   |
|   |   |   |   |   |   |   |   |   | 1 | 5 | 7 | 3 | 6 | 6 | 6 | 4 |   |   |   |   |   |   | 3 | 6 |   |
| 16 | 7 | 6 | 5 | 2 | 3 | 5 | 6 |   | 5 | 7 | 4 | 7 |   | 2 | 6 | 8 | 2 | 7 | 6 | 7 | 2 |   | 6 | 8 |   |
|   |   |   |   |   |   |   |   |   | 1 | 5 | 3 | 2 |   |   | 4 | 6 |   | 6 |   | 5 | 2 |   | 5 | 6 |   |
| 17 |   |   |   |   |   | 3 |   |   | 5 |   |   |   |   | 2 | 6 | 3 | 3 |   |   |   |   |   |   |   |   |
|   |   |   |   |   |   |   |   |   | 1 |   |   |   |   |   | 4 |   | 1 |   |   |   |   |   |   |   |   |
| 18 |   |   |   |   |   |   |   |   | 5 |   | 3 |   | 1 | 6 | 1 | 4 |   |   |   |   |   |   |   |   |   |
|   |   |   |   |   |   |   |   |   | 1 |   | 3 |   |   |   |   |   |   |   |   |   |   |   |   |   |   |
| 19 | * | * | * | * | * | * | * | * | 5 | 3 |   | 8 |   | 3 | 7 | 3 | 6 | 1 | 2 | 2 | 4 | 2 | 6 |   |   |
|   |   |   |   |   |   |   |   |   | 1 |   |   | 2 |   |   | 5 |   |   |   | 1 | 2 |   | 2 | 6 |   |   |
| 20 |   |   |   |   |   |   |   |   | 5 | 5 | 4 | 6 | 1 | 3 | 6 |   | 1 |   |   |   |   | 3 | 7 |   | 2 |
|   |   |   |   |   |   |   |   |   | 1 |   |   | 2 |   |   |   |   |   |   |   |   |   | 3 | 6 |   |   |

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg and 1 kg of active material per hectare in a volume equivalent to 900 liters per hectare in the soil spray and foliar spray test, and at a dosage of level equivalent to 10 kilograms of active material per hectare in a volume equivalent to approximately 3,000 litres per hectare in the soil drench tests.

In the pre-emergence tests untreated sown soil and in the post-emergence tests untreated soil bearing seedling plants were used as controls.

We claim:

1. A method of combating undesired plant growth at a locus, comprising applying to the locus a compound of general formula:

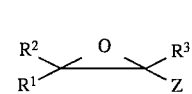

where $R^1$ and $R^2$ independently represent a hydrogen atom or an optionally substituted alkyl or alkenyl group or $R^1$ and $R^2$ together represent an optionally substituted alkyl or alkenyl chain;

$R^3$ represents an optionally substituted saturated or unsaturated homocyclic or heterocyclic group;

and Z represents a group —COOR⁴ where R⁴ represents a hydrogen atom, a cation or an optionally substituted alkyl, alkenyl, alkynyl or aryl group, or Z represents a group —CHO.

2. The method according to claim 1, wherein $R^1$ and $R^2$ independently represent a hydrogen atom, an optionally substituted alkyl group or together represent an optionally substituted alkyl chain.

3. The method according to claim 2, wherein $R^1$ and $R^2$ independently represent a hydrogen atom or a methyl group.

4. The method according to claim 1, wherein $R^3$ represents an optionally substituted phenyl group.

5. The method according to claim 4, wherein $R^3$ represents a 4-methylphenyl or 4-chlorophenyl group.

6. The method according to claim 1, wherein Z represents a group —COOR⁴ where R⁴ represents a hydrogen atom, a cation or an alkyl group.

7. A compound of general formula

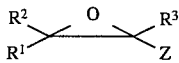   I wherein $R^1$ and $R^2$ represent a methyl group, $R^3$ represents a 4-halophenyl group, and Z represents —COONa.

8. A herbicidal composition comprising the compound of formula:

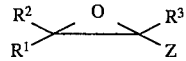   I where $R^1$ and $R^2$ independently represent a hydrogen atom or an optionally substituted alkyl or alkenyl group or $R^1$ and $R^2$ together represent an optionally substituted alkyl or alkenyl chain;

$R^3$ represents an optionally substituted saturated or unsaturated homocyclic or heterocyclic group;

and Z represents a group —COOR⁴ where R⁴ represents a hydrogen atom, a cation or an optionally substituted alkyl, alkenyl, alkynyl or aryl group, or Z represents a group —CHO, in association with at least one carrier which is a surface active agent.

9. A method of combating undesired plant growth at a locus comprising applying an effective herbicidal amount of the composition of claim 7.

10. The method according to claim 9 wherein the locus is the plant or the soil.

* * * * *